United States Patent
Murthy et al.

(10) Patent No.: US 6,380,388 B1
(45) Date of Patent: Apr. 30, 2002

(54) 1,3-OXATHIOLAN-5-ONES USEFUL IN THE PRODUCTION OF ANTIVIRAL NUCLEOSIDE ANALOGUES

(75) Inventors: K. S. Keshava Murthy, Brantford; Stephen E. Horne, Burlington; Gurijala V. Reddy, Brantford; Chandrawansha B. W. Senanayake, Brantford; Bruno K. Radatus, Brantford, all of (CA)

(73) Assignee: Brantford Chemicals Inc., Brantford (CA)

( * ) Notice: Subject to any disclaimer, the term of this patent is extended or adjusted under 35 U.S.C. 154(b) by 0 days.

(21) Appl. No.: 09/572,867

(22) Filed: May 18, 2000

(30) Foreign Application Priority Data

May 16, 2000 (CA) ............................................ 2308559

(51) Int. Cl.[7] ...................... C07D 327/04; C07D 411/04
(52) U.S. Cl. ......................................... 544/317; 549/30
(58) Field of Search ........................... 544/317; 548/30; 549/30

(56) References Cited

U.S. PATENT DOCUMENTS

| | | | |
|---|---|---|---|
| 5,204,466 A | 4/1993 | Liotta et al. | 544/317 |
| 5,210,085 A | 5/1993 | Liotta et al. | 514/274 |
| 5,466,806 A | 11/1995 | Belleau et al. | 544/310 |
| 5,486,520 A | 1/1996 | Belleau | 514/274 |
| 5,538,975 A | 7/1996 | Dionne | 514/256 |
| 5,539,116 A | 7/1996 | Liotta et al. | 544/317 |
| 5,618,820 A | 4/1997 | Dionne | 514/274 |
| 5,663,320 A | 9/1997 | Mansour et al. | 536/27.11 |
| 5,684,164 A | 11/1997 | Belleau et al. | 549/30 |
| 5,693,787 A | 12/1997 | Mansour et al. | 536/27.11 |
| 5,696,254 A | 12/1997 | Mansour et al. | 536/27.11 |
| 5,700,937 A | 12/1997 | Liotta et al. | 544/317 |
| 5,728,575 A | 3/1998 | Liotta et al. | 435/280 |
| 5,744,596 A | 4/1998 | Mansour et al. | 536/27.11 |
| 5,756,706 A * | 5/1998 | Mansour | 536/27.11 |
| 5,763,606 A | 6/1998 | Mansour et al. | 544/264 |

FOREIGN PATENT DOCUMENTS

| | | |
|---|---|---|
| WO | WO 91/11186 | 8/1991 |
| WO | WO 92/14743 | 9/1992 |
| WO | WO 00/09494 | 2/2000 |
| WO | WO 00/22157 | 4/2000 |

OTHER PUBLICATIONS

Humber, David C.; Jones, Martin F.; Payne, Jeremy J.; Ramsay, Michael V. J., Tetrahedron Lett., 33(32), 4625–8 (English) 1992.*

March, Jerry "Advanced Organic Chemistry", 1992, John Wiley, p118.*

Bouvier, P. et al., Eur.J.Med.Chem.Chim.Ther., 11, 1976, 271–278.*

(List continued on next page.)

Primary Examiner—Richard L. Raymond
Assistant Examiner—Thomas McKenzie
(74) Attorney, Agent, or Firm—Marcelo K. Sarkis; Ivor M. Hughes; Neil H. Hughes (57) ABSTRACT

A compound of the formula A,

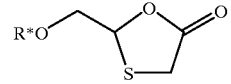

(A)

wherein R* is a chiral auxiliary, and where the configuration at the asymmetric carbon atom between oxygen and sulfur is (R), (S), or combinations of (R) and (S), useful in the preparation of enantiomerically enriched 1,3-oxathiolane nucleoside analogues, for example (−)-FTC and 3TC.

19 Claims, 3 Drawing Sheets

OTHER PUBLICATIONS

Bernard, Didier; Doutheau, Alain; Gore, Jacques, Synth.Commun., 17, 1987, 1807–1814.*

Kraus, J.–L. and Attardo, G., Synthesis, 1991, 1046–1048.*

Hoong, Lee K. et al., "Enzyme–Mediated Enantioselective Preparation of Pure Enantiomers of the Antiviral Agent 2',3'–Dideoxy–5–fluoro–3'–thiacytidine (FTC) and Related Compounds"J. Org. Chem. 1992, 57, 5563–5565.

Jeong, Lak S., et al., "Asymmetric Synthesis and Biological Evaluation of β–L–(2R,5S)– and α–L–(2R,5R)–1,3–Oxathiolane–Pyrimidine and –Purine Nucleosides as Potential Anti–HIV Agents", *J. Med. Chem.,* 1993, 36, 181–195.

J. Jacques et al., *Enantiomers, Racemates, and Resolutions,* published by John Wiley and Sons, New York, 1981.

* cited by examiner

Scheme 1

Scheme 3

Figure 3

1,3-OXATHIOLAN-5-ONES USEFUL IN THE PRODUCTION OF ANTIVIRAL NUCLEOSIDE ANALOGUES

FIELD OF THE INVENTION

The present invention relates to commercial processes for the production of antiviral 1,3-oxathiolane nucleoside analogues including, but not limited to, cis(−)-4-amino-5-fluoro-1-[2-(hydroxymethyl)-1,3-oxathiolan-5-yl]-2(1H)-pyrimidinone (emtricitabine, (−)-FTC, 1) and cis(−)-4-amino-1-[2-(hydroxymethyl)-1,3-oxathiolan-5-yl]-2(1H)-pyrimidinone (lamivudine, 3TC, 2). In one embodiment, the present invention relates to novel crystalline intermediates useful in the preparation of antiviral 1,3-oxathiolane nucleoside analogues in enantiomerically enriched form, and to commercial processes for their preparation.

BACKGROUND OF THE INVENTION

Nucleoside analogues are well known therapeutic agents, often displaying antiviral activity against retroviruses such as human immunodeficiency virus (HIV), hepatitis B virus (HBV), and human T-lymphotropic virus (HTLV). Generally speaking, nucleoside analogues can exist in two distinct stereoisomeric forms, known as cis and trans diastereomers. However, it is usually only the cis diastereomers of nucleoside inhibitors which display significant biological activity. Each cis and trans diastereomer is further composed of two pairs of stereoisomers, known as enantiomers. For many nucleoside analogues, including (−)-FTC and 3TC, the antiviral activity is significantly more pronounced in one of two possible enantiomeric forms of the cis diastereomer. In the case of (−)-FTC and 3TC, the levorotatory, or (−), enantiomer is the major contributor to the desired antiviral activity, as is disclosed in the following: U.S. Pat. Nos. 5,486,520; 5,539,116; J. Org. Chem. 1992, 57, 2217–2219; J. Med. Chem. 1993, 36, 181–195. Consequently, commercial manufacturing methods which are capable of producing nucleoside analogues in enantiomerically enriched form are of primary importance for the continued chemical and pharmaceutical development of such 1,3-oxathiolane nucleoside analogues.

The prior art discloses several methods for the preparation of 1,3-oxathiolane nucleoside analogues by processes which do not address the issue of enantioselectivity and, consequently, provide 1,3-oxathiolane nucleoside analogues as mixtures of enantiomers. Examples of such methods for obtaining 1,3-oxathiolane nucleoside analogues as diastereomeric and/or enantiomeric mixtures may be found in U.S. Pat. No. 5,204,466 "Method and Compositions for the Synthesis of BCH-189 and Related Compounds", U.S. Pat. No. 5,210,085 "Method for the Synthesis, Compositions, and Use of 2'-Deoxy-5-fluoro-3'-thiacytidine and Related Compounds", U.S. Pat. No. 5,466,806 "Process for Preparing Substituted 1,3-Oxathiolanes with Antiviral Properties" and U.S. Pat. No. 5,763,606 "Stereoselective Synthesis of Nucleoside Analogues Using A Bicyclic Intermediate". Such processes have obvious limitations for commercial production purposes since the degree of enantioselectivity imparted into the finished active compound is marginal or absent.

On the other hand, U.S. Pat. No. 5,728,575 ("Method of Resolution of 1,3-Oxathiolane Nucleoside Enantiomers") describes the preparation of nucleoside analogues, including (−)-FTC, in enantiomerically enriched form using a process involving enzyme mediated hydrolysis of a racemic mixture of nucleoside analogue esters. Enzymes employed are selected from the group consisting of pig liver esterase (PLE), pig pancreatic lipase (PPL), and substillisin. Esters are selected from the group consisting of acetate, propionate, butyrate, and pentanoate. The enzyme preferentially catalyzes the hydrolysis of an ester group in one of the two enantiomers, allowing a subsequent separation of unhydrolyzed nucleoside analogue ester and hydrolyzed nucleoside analogue. The process can be depicted as follows:

+

While the degree of recognition displayed by the enzyme for hydrolysis of one enantiomer over the other is very high, the resolution of enantiomers occurs at a very late stage in the overall process to the nucleoside analogue. This is an undesirable situation from a commercial production and economic standpoint because the resolution of enantiomers of the 1,3-oxathiolane nucleoside analogue occurs in the penultimate step of the process therefore results in, at minimum, fifty percent loss of the batch material. Secondly, enzymatic hydrolysis occurs on the undesired enantiomer preferentially, which necessitates a subsequent hydrolysis step on the separated desired enantiomer to completely form the desired nucleoside analogue. The consequences of this additional step are increased manufacturing overhead costs and loss of material through non-stoichiometric conversion. Furthermore, the possibility of recovering the undesired enantiomer and recycling it into the process to form the desired enantiomer becomes highly improbable to complete in an economical manner due to the inherent challenge of simultaneously epimerizing the two stereocentres from one cis conformation to the second (desired) cis conformation. Finally, the introduction of impurities in the finished product, originating from the enzyme preparation itself, is a major concern since the enzymatic resolution occurs in the penultimate step of the process.

Published PCT application WO 00/09494 discloses processes for the preparation of 1,3-oxathiolane nucleoside analogues which, when used in conjunction with the prior art, may be used to produce enantiomerically enriched 1,3-oxathiolane nucleoside analogues, including (−)-FTC.

U.S. Pat. No. 5,663,320 "Processes for the Diastereoselective Separation of Nucleoside Analogue Synthetic Intermediates", U.S. Pat. No 5,684,164 "Processes for Preparing Substituted 1,3-Oxathiolanes With Antiviral Properties", U.S. Pat. No. 5,693,787 "Intermediates in the Synthesis of 1,3-Oxathiolanyl Cytosine Nucleoside Analogues", U.S. Pat. No. 5,696,254 "Processes for the Diastereoselective Synthesis of Nucleoside Analogues" U.S. Pat. No. 5,744,596 "Nucleoside Analogues and Synthetic Intermediates", and U.S. Pat. No. 5,756,706 "Processes for the Diastereoselective Synthesis of Nucleoside Analogues", describe processes for the enantioselective preparation of nucleoside analogues, including 1,3-oxathiolane nucleoside analogues. For example, one such process involves the use of enantiomerically enriched intermediates of the form where R is a chiral auxiliary, and L is a leaving group. Preferred chiral auxiliaries in this case are selected from (+) and (−)-menthol and (+) and (−)-norephedrine. Prior to the conversion of such intermediates into 1,3-oxathiolane nucleoside analogues, reduction of the substituted carbonyl group to a hydroxymethyl group is required. This may lead to undesired racemization of the 1,3-oxathiolane nucleoside analogue during chemical reduction thus resulting in economic and material loss, and necessitating further processing to arrive at material of pharmaceutically acceptable purity.

An improved method for the obtention of 1,3-oxathiolane nucleoside analogues is therefore required as there continues to exist an ongoing requirement to produce the therapeutically important antiviral agents, such as (−)-FTC and 3TC, using safe, efficient, and economical commercial processes avoiding the drawbacks of the prior art discussed above.

It is therefore an object of the invention to provide an improved process for obtaining 1,3-oxathiolane nucleoside analogues and intermediates useful in the obtention thereof which overcomes the disadvantages of the prior art.

Furthermore, it is an object of the invention to provide novel intermediates useful in the process for obtaining the 1,3-oxathiolane nucleoside analogues and intermediates useful in the obtention thereof. It is still a further object of the invention to provide novel intermediates useful in the manufacture of the 1,3-oxathiolane nucleoside analogues. It is still a further object of the invention to provide a process for the manufacture of the novel intermediates in enantiomerically enriched form.

Further and other objects of the invention will be apparent to those skilled in the art from the following summary of invention and the detailed description of embodiments thereof.

SUMMARY OF THE INVENTION

It has now been found that compounds of the general formula A (A)

wherein R* is a chiral auxiliary, and preferably in one instance, the configuration at the asymmetric carbon atom between oxygen and sulfur is (R), (S), or combinations of (R) and (S), and preferably within the scope of compounds within the formula A, compounds of the general formula B (B)

wherein $R_3$ is either a chiral or an achiral auxiliary, and preferably in one instance the configuration at the asymmetric carbon atom between oxygen and sulfur is (R), (S), or combinations of (R) and (S), are useful in the production of 1,3-oxathiolane nucleoside analogues, as described below. The substituents R* and $R_3$ are such that they permit the compounds (A) or (B) to react in the processes to make 1,3-oxathiolane nucleoside analogues or any intermediate useful in the manufacture of 1,3-oxathiolane nucleoside analogues and do not interfere in the manufacture thereof.

Many techniques such as chromatographic separation or distillative separation are known to be useful in the non-chemical based resolution of stereoisomers. By industrial practice, the obtention of enantiomerically enriched pharmaceutical intermediates and active ingredients continues to rely heavily upon selective crystallization of diastereomeric compounds because of economic advantages and the use of standardized equipment (see J. Jacques et al., *Enantiomers, Racemates, and Resolutions,* John Wiley and Sons, New York, 1981). Crystallization based processes are especially desirable when the possibility of recovering and recycling of undesired stereoisomers exists. The discovery of such novel intermediates A and B, crystalline in form, and their purification via recrystallization techniques, allows the removal of their undesired stereoisomers and of other process derived impurities which might be otherwise difficult to remove at later stages of commercial manufacturing.

Therefore, according to one aspect of the invention, a process for the industrial synthesis of intermediates useful in the preparation of 1,3-oxathiolane nucleoside analogues, in enantiomerically enriched form, is disclosed. The discovery of such novel, enantiomerically enriched intermediates permits their coupling to a variety of base partners to provide 1,3-oxathiolane nucleoside analogues, including, but not limited to, (−)-FTC and 3TC, in enantiomerically enriched form.

Therefore, according to one aspect of the invention there is provided a compound of the formula A, (A)

wherein R* is a chiral auxiliary, preferably the configuration at the asymmetric carbon atom between oxygen and sulfur is (R), (S), or combinations of (R) and (S), wherein compound of formula (A) is useful in the preparation of enantiomerically enriched 1,3-oxathiolane nucleoside analogues.

According to another aspect of the invention, there is provided a compound of formula B, (B)

wherein $R_3$ is a chiral or achiral auxiliary, preferably the configuration at the asymmetric carbon atom between oxygen and sulfur is (R), (S), or combinations of (R) and (S), wherein the compound of formula (B) is useful in the preparation of enantiomerically enriched 1,3-oxathiolane nucleoside analogues.

According to another aspect of the invention, there is provided a process for the manufacture of a compound of the formula A (A)

wherein R* is a chiral auxiliary, preferably the configuration at the asymmetric carbon atom between oxygen and sulfur is (R), (S), or combinations of (R) and (S), said process comprising the following:

Preferably the compound of formula A is (B)

wherein $R_3$ is selected from the group consisting of a chiral or achiral auxiliary, preferably the configuration at the asymmetric carbon atom between oxygen and sulfur is (R), (S), or combinations of (R) and (S). Preferably said compound is

9

Preferably the chiral or achiral auxiliary permits the compound to react in the process to make a 1,3-oxathiolane nucleoside analogue or any intermediate useful in the manufacture of a 1,3-oxathiolane nucleoside analogue. Preferably the chiral auxiliary is a chiral auxiliary derived from a carboxylic acid or derivatives thereof. Preferably the chiral auxiliary is selected from the group consisting of mandelic acid, menthoxyacetic acid, amino acids, camphorsulphonic acid, 2-arylpropionic acids, enantiomers thereof, preferably enantiomerically enriched forms thereof and derivatives thereof.

According to yet another aspect of the invention there is provided use of a compound of the formula A (A)

wherein R* is a chiral auxiliary, preferably the configuration at the asymmetric carbon atom between oxygen and sulfur is (R), (S), or combinations of (R) and (S), in the preparation of enantiomerically enriched 1,3-oxathiolane nucleoside analogues or derivatives thereof or intermediates useful in the manufacture of 1,3-oxathiolane nucleoside analogues. Preferably the 1,3-oxathiolane nucleoside analogues or derivatives thereof or intermediates useful in the manufacture of 1,3-oxathiolane nucleoside analogues are enantiomerically enriched. Preferably the compound of formula A is (B)

wherein $R_3$ is selected from the group consisting of a chiral or achiral auxiliary, preferably the configuration at the asymmetric carbon atom between oxygen and sulfur is (R), (S), or combinations of (R) and (S). More preferably the compound of formula A is

9

According to yet another aspect of the invention, there is provided a process for the manufacture of compound of formula

9 useful as an intermediate for conversion into an enantiomerically enriched 1,3-oxathiolane nucleoside analogue, comprising the reaction of mandelic acid with a compound of formula 4

4 wherein X is a leaving group, preferably halogen, more preferably chlorine or bromine, to produce a compound of formula 5,

5 and thereafter converting the compound of formula 5 into the intermediate of formula 9 preferably in a substantially high purity, crystalline form, preferably by the steps of halogenation, esterification, lactonization, and selective crystallization. Preferably the step of halogenation involves conversion of (2S)-2-(trimethylacetyloxy)phenylacetic acid into a (2S)-2-(trimethylacetyloxy) phenylacetyl halide; preferably the step of esterification involves reacting the (2S)-2-trimethylacetyloxy)phenylacetyl halide with a 2,2-dialkoxyethanol compound to produce a 2,2-dialkoxyethyl (2S)-2-(trimethylacetyloxy)phenylacetate; preferably the step of lactonization involves reacting the 2,2-dialkoxyethyl (2S)-2-(trimethyl-acetyloxy)phenylacetate intermediate with 2-mercaptoacetic acid to produce a mixture of (2R)-2-[(2'S)-2'-(trimethylacetyloxy)phenylacetyloxymethyl]-1,3-oxathiolan-5-one and (2S)-2-[(2'S)-2'-(trimethylacetyloxy) phenylacetyloxy methyl]-1,3-oxathiolan-5-one; and preferably the step of selective crystallization involves the separation of (2R)-2-[(2'S)-2'-(trimethylacetyloxy) phenylacetyloxymethyl]-1,3-oxathiolan-5-one from (2S)-2-[(2'S)-2'-(trimethylacetyloxy)phenylacetyloxymethyl]-1,3-oxathiolan-5-one mixture to produce enantiomerically and diastereomerically enriched (2R)-2-[(2'S)-2'-(trimethylacetyloxy)phenylacetyloxy methyl]-1,3-oxathiolan-5-one; preferably the trimethylacetyl halide is trimethylacetyl chloride; preferably still the (2S)-2-(trimethylacetyloxy)phenylacetyl halide is (2S)-2-(trimethylacetyloxy)phenylacetyl chloride.

According to yet another aspect of the invention, there is provided (2R) and (2S)-2-[(2'S)-2'-(Trimethylacetyloxy) phenylacetyloxymethyl]-1,3-oxathiolan-5-one.

Preferably the intermediate of formula 9 produced above is further converted to the desired 1,3-oxathiolane nucleoside analogue, preferably 3TC or (−)-FTC.

According to yet another aspect of the invention there is provided a process for converting an intermediate of formula (A) to a 1,3-oxathiolane nucleoside analogue preferably by the process which involves the steps of acylation, preferably reductive acylation, coupling with a base, and hydrolysis. Preferably the 1,3-oxathiolane nucleoside analogue is (−)-FTC, or 3TC.

According to yet another aspect of the invention there is provided a process for the recovery and recycling of (2S)-2-[(2'S)-2'-(trimethylacetyloxy) phenylacetyloxymethyl]-1, 3-oxathiolan-5-one.

According to yet another aspect of the invention there is provided a process of preparing a compound of the formula (2R)-A comprising the following:

or activated derivative thereof
R* = chiral auxiliary

$R_1, R_2$ = alkyl, cycloalkyl, aryl, heterocyclic, alkaryl, aralkyl

According to yet another aspect of the invention there is provided use of a compound of the formula (2R)-A in the manufacture of a 1,3-oxathiolane nucleoside analogue or enantiomerically enriched intermediate thereof.

According to yet another aspect of the invention there is provided a process of preparing a 1,3-oxathiolane nucleoside analogue comprising the following:

1,3-oxathiolane nucleoside analogue

According to yet another aspect of the invention there is provided a process of preparing a 1,3-oxathiolane nucleoside analogue comprising the following:

BRIEF DESCRIPTION OF THE DRAWINGS

The following figures illustrate preferred and alternative embodiments of the invention, wherein.

DISCUSSION OF ASPECTS AND EMBODIMENTS OF THE INVENTION

There is provided a compound of the formula A (A)

wherein R* is a chiral auxiliary, preferably a chiral auxiliary derived from a carboxylic acid or derivative thereof, preferably the configuration at the asymmetric carbon atom between oxygen and sulfur is (R), (S), or combinations of (R) and (S). Some examples of chiral auxiliaries include mandelic acid and derivatives thereof, menthoxyacetic acid, various natural and unnatural amino acids and their derivatives, camphorsulphonic acid, and 2-arylpropionic acids. Other chiral auxiliaries or derivatives thereof that permit the compounds to react in any process to make a 1,3-oxathiolane nucleoside analogue or any intermediate useful in the manufacture of a 1,3-oxathiolane nucleoside analogue are also within the scope of the present invention and the selection of chiral auxiliaries is not limited by the above examples.

Figure 1:
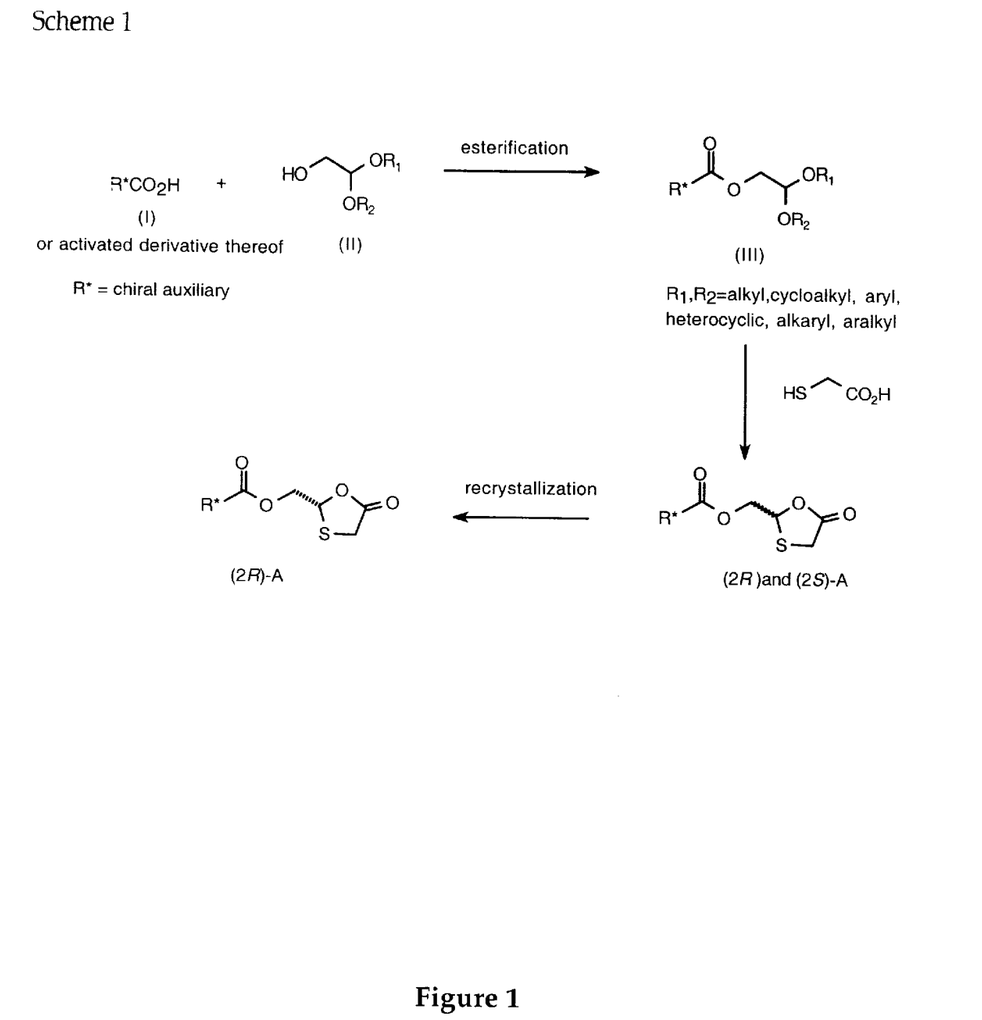
FIG. 1 is a scheme (Scheme 1) of one embodiment of the present invention.

Broadly, a process is disclosed for the manufacture of a enantiomerically enriched compound of formula (A) suitable for conversion into a 1,3-oxathiolane nucleoside analogue. There is found in one embodiment a process to manufacture a novel intermediate useful in one instance in the manufacture of 1,3-oxathiolane nucleoside analogues and intermediates thereof. Looking to FIG. 1, there is shown Scheme 1, which comprises reacting a chiral auxiliary (R*CO$_2$H, I), or a derivative thereof, with a 2,2-dialkoxyethanol derivative (II) to produce an ester (III), and thereafter converting said ester III into a mixture of (2R) and (2S) diastereomers of the compound of formula (A) by reacting III with 2-mercaptoacetic acid or a derivative thereof, and finally crystallizing the resultant mixture of (2R) and (2S)-A from solution. Recrystallization of (2R) and (2S)-A is then carried out until the desired level of diastereomeric and enantiomeric purity of (2R)-A is achieved. For example, when the required 1,3-oxathiolane nucleoside analogue under consideration is (−)-FTC, a 96% enantiomeric excess of (2R)-A is currently preferred.

Figure 2:
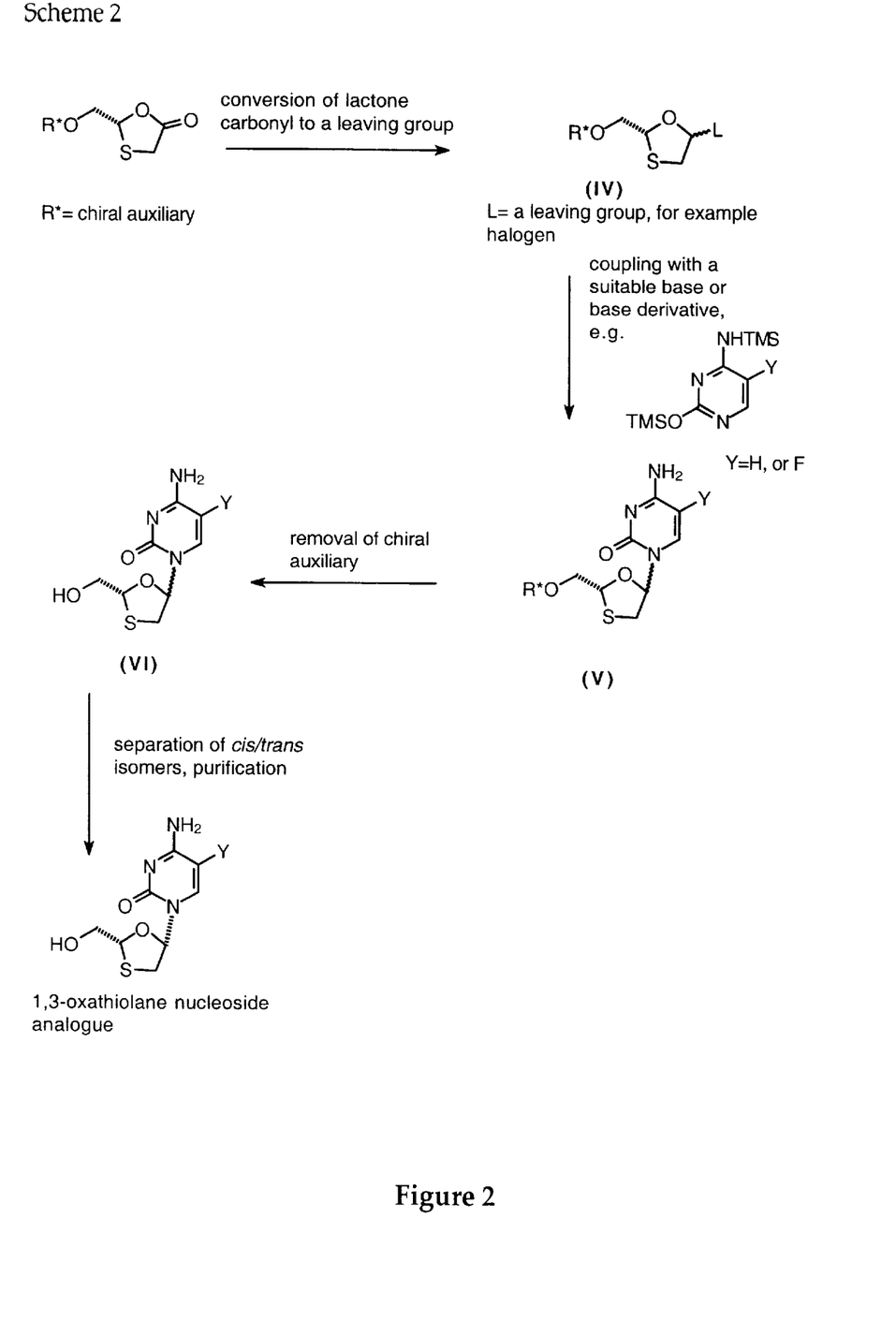
FIG. 2 is a scheme (Scheme 2) of another embodiment of the present invention.

According to another aspect of the invention, there is provided a process for manufacturing a 1,3-oxathiolane nucleoside analogue which in one embodiment is depicted in FIG. 2 which depicts Scheme 2, which comprises converting the lactone carbonyl moiety of enantiomerically enriched compound (2R)-A into a leaving group, followed by the coupling of the intermediate (IV) so produced with an appropriate organic base or derivative thereof such that a protected 1,3-oxathiolane nucleoside analogue (V) is produced. Thereafter, removal of the chiral auxiliary in (V) using any suitable method, for example, one of several standard hydrolytic methods, produces a compound of formula VI as a mixture of cis and trans diastereomers, which may be separated to produce the desired cis diastereomer of the 1,3-oxathiolane nucleoside analogues.

Figure 3:
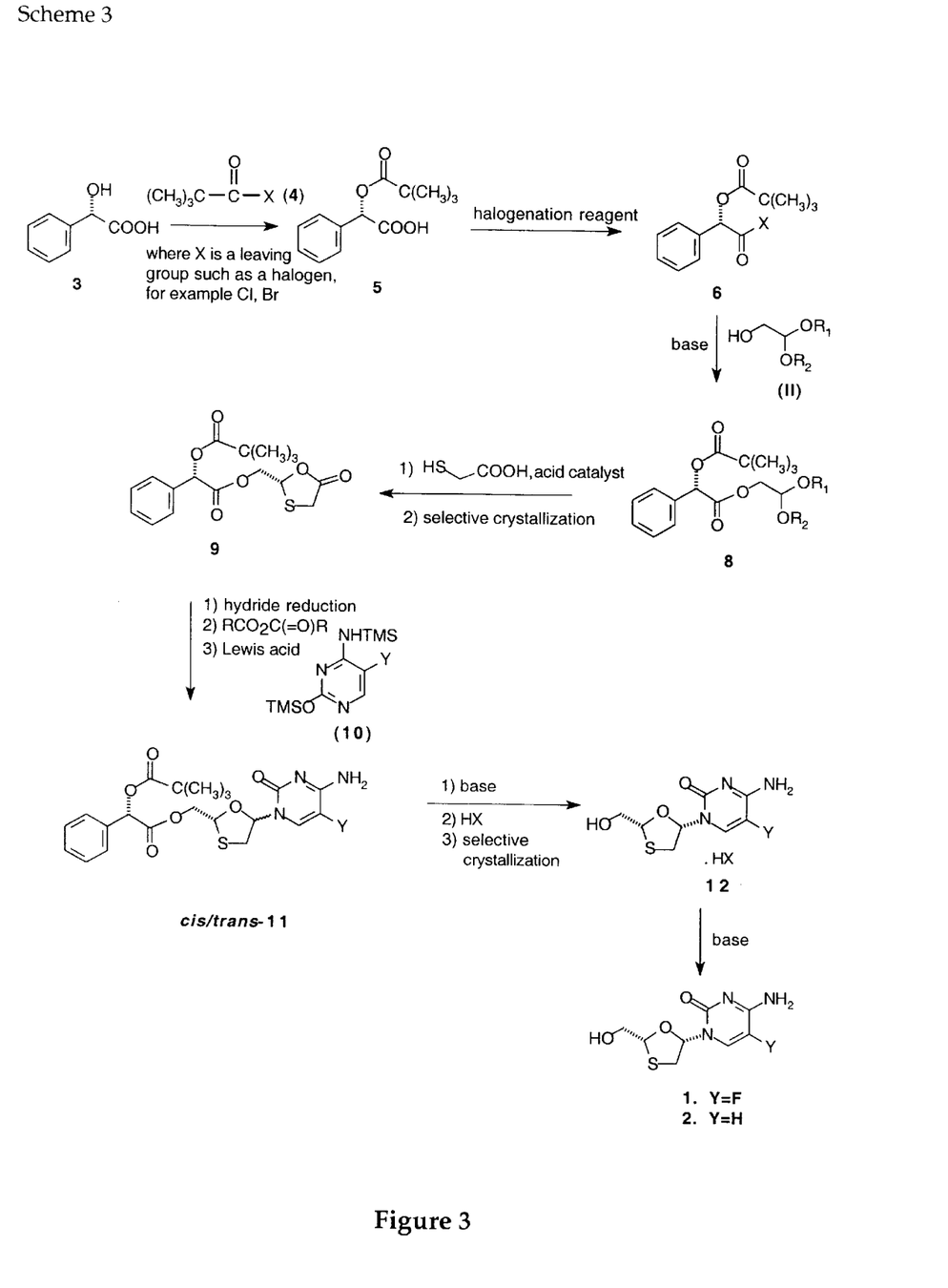
FIG. 3 is a scheme (Scheme 3) of another embodiment of the present invention.

According to another aspect of the invention as best seen in FIG. 3, there is provided as Scheme 3 the acylation of (S)-(+)-mandelic acid (3) at its alcohol moiety with a trimethylacetyl halide (4) to produce (2S)-2-(trimethylacetyloxy)phenylacetic acid (5). The carboxylic acid portion of (5) is next converted into a (2S)-2-(trimethylacetyloxy)phenylacetyl halide (6). The acyl halide (6) is reacted with a 2,2-dialkoxyethanol compound (II), in the presence of a suitable base such as imidazole, to produce a 2', 2'-dialkoxyethyl (2S)-2-(trimethylacetyloxy) phenylacetate intermediate (8). Reaction of the compound 8 with 2-mercaptoacetic acid, preferably catalyzed by an acid, preferably an organosulphonic acid, produces a mixture of (2R)-2-[(2'S)-2'-(trimethylacetyloxy)phenyl acetyloxymethyl]-1,3-oxathiolan-5-one(2S) and (2S)-2-[(2'S)-2'-(trimethylacetyloxy) phenylacetyloxymethyl]-1,3-oxathiolan-5-one. Selective crystallization of the mixture of (2R)-2-[(2'S)-2'-(trimethylacetyloxy) phenylacetyloxymethyl]-1,3-oxathiolan-5-one (9) and (2S)-2-[(2'S)-2'-(trimethylacetyloxy)phenylacetyloxymethyl]-1,3-oxathiolan-5-one, for example using isopropanol and/or mixtures of isopropanol and water, or mixtures of toluene and heptanes, produces the compound 9, possessing predominantly the (2R) configuration, as determined by single crystal x-ray diffraction, in the 1,3-oxathiolan-5-one ring, in high chemical, diastereomeric and enantiomeric purity.

The processes of this invention allow for the preparation of an intermediate, for example compound (9) found in FIG. 3 useful in the synthesis of 1,3-oxathiolane nucleoside analogues, such as (−)-FTC and 3TC, by advantageously using inexpensive raw materials and high-yielding, industrially feasible reactions and represent improved methods over the prior art for obtaining enantiomerically enriched intermediates for the production of 1,3-oxathiolane nucleoside analogues.

The methods described herein allow for recovery of the undesired stereoisomer of the compound 9, that is [(2S)-2-[(2'S)-2'-(trimethylacetyloxy)phenylacetyloxymethyl]-1,3-oxathiolan-5-one, from the crystallization mother liquor, and for its epimerization at the 2-position of its 1,3-oxathiolane ring, thus allowing its eventual recycling into the desired stereoisomer of the intermediate, for example compound (9) by repetition of the selective crystallization process.

The processes of the invention also allow for the recovery of the chiral auxiliary, in this example mandelic acid, following its ultimate hydrolytic removal from the 1,3-oxathiolane nucleoside analogue. Thus, in this manner the overall economic and industrial feasibility of the manufacturing 1,3-oxathiolane nucleoside analogues by this process are further enhanced.

Enantiomerically enriched compound (9) of Scheme 3 in FIG. 3 is readily converted into 1,3-oxathiolane nucleoside analogues. For example, reductive acylation of compound (9) chemoselectively at the lactone carbonyl group produces a (2R)-2-[(2'S)-2'-(trimethyl acetyloxy) phenylacetyloxymethyl]-5-acyloxy-1,3-oxathiolane. Coupling of the resulting (2R)-2-[(2'S)-2'-(trimethylacetyloxy) phenylacetyloxymethyl]-5-acyloxy-1,3-oxathiolane with an appropriate base, for example, a persilylated pyrimidine base (10) preferably in the presence of a Lewis acid produces a mixture of cis and trans isomers of a 4-amino-1-[2-{(2'S)-2'-(trimethylacetyloxy)phenylacetyloxymethyl}-1,3-oxathiolan-5-yl]-2(1H)-pyrimidinone derivative (cis/trans-11). If desired, the hydrolysis of the cis and trans mixture (cis/trans-11) followed by salt formation and preferential crystallization provides an enantiomerically and diastereomerically enriched salt of the 1,3-oxathiolane nucleoside analogue (12). The compounds of formula 12 may be converted to their free base forms and further purified by conventional crystallization to provide the desired 1,3-oxathiolane nucleoside analogues (1 and 2) with acceptable pharmaceutical purity.

Therefore, according to an aspect of the invention, novel economical manufacturing processes for the production of 1,3-oxathiolane nucleosides, including (−)-FTC and 3TC have been provided.

Further, according to another aspect of this invention, there is provided the use of a crystalline, enantiomerically enriched compound 9, of high chemical purity, in the manufacture of 1,3-oxathiolane nucleoside analogues, including (−)-FTC and 3TC.

A preferred process of the present invention appears in FIG. 3 depicting Scheme 3. Acylation of (S)-(+)-mandelic acid (3) in the neat state or in a suitable solvent, preferably toluene, with a trimethylacetyl derivative, preferably trimethylacetyl chloride (4, X=Cl), occurs to form (2S)-2-(trimethylacetyloxy)phenylacetic acid (5). The conversion of compound 5 to the corresponding acid halide, preferably (2S)-2-(trimethylacetyloxy)phenylacetyl chloride (6, X=Cl), is conducted by heating with a suitable halogenation reagent, preferably thionyl chloride, optionally in the presence of a suitable catalyst, in a suitable solvent, preferably toluene, at elevated temperatures, preferably 30–60° C. The aforementioned acid halide compound is reacted with a 2,2-dialkoxyethanol derivative, preferably 2,2-dimethoxyethanol (II, $R_1$=$R_2$=Me), in the presence of an appropriate base, preferably imidazole, to produce a 2',2'-dialkoxyethyl (2S)-2-(trimethylacetyloxy)phenylacetate intermediate (8, $R_1$=$R_2$=Me). The reaction is conducted in a suitable organic solvent, preferably toluene, at temperatures below ambient room temperature, preferably −20–+10° C. Reaction of the intermediate 8 with 2-mercaptoacetic acid in the presence of a Bronsted or Lewis acid catalyst, preferably camphorsulphonic acid, in a suitable organic solvent, preferably toluene, at elevated temperatures, preferably at temperatures of 45–65° C., produces a mixture of (2R)-2-[(2'S)-2'-(trimethylacetyloxy)phenylacetyloxymethyl]-1,3-oxathiolan-5-one and (2S)-2-[(2'S)-2'-(trimethylacetyloxy)phenyl acetyloxymethyl]-1,3-oxathiolan-5-one. Selective crystallization of the mixture of (2R)-2-[(2'S)-2'-(trimethylacetyloxy) phenylacetyloxymethyl]-1,3-oxathiolan-5-one and (2S)-2-[(2'S)-2'-(trimethylacetyloxy)phenylacetyloxymethyl]-1,3-oxathiolan-5-one is conducted in a mixture of organic solvent, preferably heptanes/toluene (2/1), which maximizes the difference in solubility between the two diastereomers, at temperatures from which the desired diastereomer 9, possessing the predominantly (2R) absolute configuration in the 1,3-oxathiolan-5-one ring, is recovered in optimal yield. In the present invention, the preferred optimal batch temperature for isolation lies between 20–40° C.

The conversion of the compound (9) to 1,3-oxathiolane nucleoside analogues, for example (−)-FTC or 3TC, may be carried out as depicted in Scheme 3. Reductive acylation of the compound (9) chemoselectively at the lactone carbonyl group with a reducing agent, in an organic solvent, produces a (2R)-2-[(2'S)-2'-(trimethylacetyloxy) phenylacetyloxymethyl]-5-acyloxy-1,3-oxathiolane. Coupling of the unisolated (2R)-2-[(2'S)-2'-(trimethylacetyloxy) phenylacetyloxymethyl]-5-acyloxy-1,3-oxathiolane, in an organic solvent, with for example a persilylated pyrimidine base (10) in the presence of a Lewis acid, produces a mixture of cis and trans diastereomers of the compound of formula (11). Hydrolysis of the cis and trans mixture of compound (11) using a base, followed by the addition of a suitable acid, results in crystallization of the diastereomerically enriched salt of the 1,3-oxathiolane nucleoside analogue (12), which is recrystallized to provide pure cis isomer 12. Conversion of the salt (12) to the free base form of the enantiomerically enriched pharmaceutically pure nucleoside analogue (1 or 2) can be carried out in a suitable solvent with an organic or inorganic base.

EXAMPLES

The following examples serve to illustrate embodiments of the present invention in a manner in which they can be practised but, as such, should not be considered in a limiting sense.

Example 1

(a) (2S)-2-(Trimethylacetyloxy)phenylacetyl Chloride (6, X=Cl)

A 3-necked, 1 L flask equipped with a mechanical stirrer, thermometer and nitrogen inlet and outlet to a dilute caustic scrubber is loaded with (S)-(+)-mandelic acid (3) (50.92 g), toluene (102 mL) and trimethylacetyl chloride (4, X=Cl) (49.98 g, 51 mL). The mixture is heated to 48–52° C. and maintained for 8 hours with a nitrogen purge to help remove the released hydrogen chloride gas. The clear solution is cooled to 28–32° C. and toluene (51 mL) and dimethylformamide (3% wt) are added. To this mixture thionyl chloride (83.13 g, 51 mL) is added in 6 portions over 1 hour. During the reaction a nitrogen purge is maintained to help remove the release of hydrogen chloride. During the next 75 minutes, the temperature is increased to 30–38° C. and maintained at that temperature for an additional 2 hours. The mixture is cooled to room temperature and then vacuum distilled to remove toluene, trimethylacetyl chloride and thionyl chloride. Additional toluene (51 mL) is added and the solution is vacuum distilled to an oil.

$^1$H NMR (300 MHz, CDCl$_3$): 1.31 (s, 9H,), 6.06 (s, 1H), 7.44–7.53 (m, 5H).

(b) (S)-(+)-Camphorsulfonyl Chloride

A 500 mL, 3-necked flask equipped with a condenser, an air trap, and a 10% sodium hydroxide trap is loaded with camphorsulfonic acid (23.23 g). To the reaction mixture is added thionyl chloride (47.59 g, 30 mL). The mixture is heated to reflux using an oil bath. The solution was allowed to cool to 25° C. and poured onto crushed ice (200 g). The obtained crystals are filtered, washed with cold water (2×20 mL), dried under high vacuum to give 22 g of (S)-(+)-camphorsulfonyl chloride.

(c) (S)-6-Methoxy-α-methyl-2-naphthaleneacetyl Chloride

A mixture of (S)-6-methoxy-α-methyl-2-naphthaleneacetic acid (23.09 g) and THF (41 mL) is agitated until dissolution is achieved. Oxalyl chloride (17.5 mL) is added to the flask followed by DMF (3 drops) and heptanes (50 mL). The mixture is stirred for approximately 2 hours. The resulting slurry is filtered, washed with heptane (15 mL) and aspirated for 3 minutes and vacuum dried to give 17.44 g.

d) (2S)-2-(Acetyloxy)phenylacetyl Chloride

A 250 mL, round bottom flask equipped with a stir bar and a 10% sodium hydroxide trap is charged with S-(+)-mandelic acid (35 g) and acetyl chloride (50.3 g) (slowly, 5–10 min.) at 20–25° C. The mixture is stirred for 2–3 hours and vacuum distilled (40–45° C.) to remove excess acetyl chloride. The resulting syrup was further dried under high vacuum for 16 hours. To the resulting semi-solid is added thionyl chloride (84 g) at 20–25° C. The reaction is maintained at 20–25° C. until a clear solution is formed. The mixture is refluxed for 3 hours and then distilled to remove excess thionyl chloride to provide 40 g of product.

Example 2

(a) 2,2-Dimethoxyethyl (2S)-2-(Trimethylacetyloxy) phenylacetate (8, R$_1$=R$_2$=Me)

The glass-lined reactor (100 L) is loaded with toluene (29 kg), 2,2-dimethoxyethanol (II, R$_1$=R$_2$=CH$_3$) (1.81 kg) and imidazole (2.23 kg). The batch is agitated and cooled to −2° C. to 2° C. The acid chloride (6, X=Cl) (3.34 kg) dissolved in toluene (6.0 kg) is added to the alcohol mixture in portions so as to maintain the temperature below 5° C. Portions of about 100–500 g can be used initially and the addition will take about 30 minutes. Cooling is removed and the reactor is allowed to warm to room temperature over 2 hours and maintained at room temperature for 4 hours. Water (20 kg) is loaded into the reactor followed by 4% hydrochloric acid (17.95 kg) in portions until the pH of the aqueous phase is 1.0–2.0. The aqueous phase is separated and back-extracted with toluene (8.65 kg). The combined toluene phases are washed with water (20 kg), saturated sodium bicarbonate (10 kg) and 10% aqueous acetic acid (10 kg). The toluene phase is vacuum distilled to provide an oil.

$^1$H NMR (300 MHz, CDCl$_3$): 1.29 (s, 9H), 3.27 (s, 3H), 3.28 (s, 3H), 4.06–4.19 (m, 2H), 4.46 (t, J=5.4, 1H), 5.90 (s, 1H), 7.37–7.51 (m, 5H).

(b) 2,2-Diethoxyethyl (S)-(+)-Camphorsulfonate 2,2-Diethoxyethanol (3.82 g), Et$_3$N (3.17 g), dichloromethane (40 mL) and DMAP (4 mg) are combined and the solution is cooled to 4° C. (S)-Camphorsulfonyl chloride (7.5 g) is added at a rate of 1 g /min. The ice-water bath is removed and the reaction is allowed to progress for about 1 hour at room temperature. About 40 mL of water is added slowly to quench the reaction, the phases are separated and the dichloromethane phase is washed with saturated sodium bicarbonate (20 mL) and water (20 mL). The solution is vacuum concentrated to produce 7.9 g of 2,2-diethoxyethyl (S)-(+)-camphorsulfonate.

(c) 2,2-Dimethoxyethyl (S)-6-Methoxy-α-methyl-2-naphthaleneacetate 2,2-Dimethoxyethanol (8.12 g), Et$_3$N (8.99 g), DMAP (80 mg) and toluene (71 mL) are combined and stirred at room temperature. (S)-6-Methoxy-α-methyl-2-naphthaleneacetyl chloride (18.42 g) is added in portions over a period of 8 minutes. The resulting slurry is agitated (35–40° C.) until the reaction is judged to be complete. To the reaction mixture is added water (80 mL) and the phases are separated. The toluene phase is washed with saturated sodium bicarbonate (40 mL) and water (40 mL) and concentrated. Dichloromethane (20 mL) is added and the vacuum evaporation is repeated to produce 21.20 g of 2,2-dimethoxyethyl (S)-6-methoxy-α-methyl-2-naphthaleneacetate.

(d) 2,2-Diethoxyethyl (2S)-2-(Acetyloxy) phenylacetate

A 3-necked, 250 mL, round bottom flask equipped with a stir bar and a condenser is charged with 2,2-diethoxyethanol (10 g), dry methylene chloride (100 mL) and triethylamine (9 g). The mixture is cooled to 0–5° C. over a period of 1–2 hours. The flask is slowly charged with (2S)-2-(acetyloxy)

phenylacetyl chloride (16.6 g) while maintaining IT<10° C. over a period of 0.5–1 hour. The reaction is stirred at 15–20° C. for 1–2 hours. The reaction mixture is filtered and the filter cake is washed with dichloromethane (10 mL). The organic layer is transferred to a separatory funnel and washed with deionized water (2×40 mL) followed by brine (1×30 mL). The organic layer is dried over anhydrous sodium sulfate and evaporated to give 21 g of 2,2-diethoxyethyl (2S)-2-(acetyloxy)phenylacetate as a syrup.

(e) 2,2-Dimethoxyethyl N-Benzyloxycarbonyl-L-prolinate

To a 100 mL, round bottom flask equipped with a magnetic stirrer and nitrogen inlet is added N-Benzyloxycarbonyl-L-proline (3.5 g), dichloromethane (25 mL) and 2,2-dimethoxyethanol (1.8 g). The mixture is cooled using an ice bath (0–5° C.) and DMAP (86 mg) is added. DCC (3.06 g) is added to the mixture over a period of 2 minutes. The resulting precipitate is filtered, washed with heptanes (2×10 mL) and the filtrate is concentrated under reduced pressure. The residue was purified by silica gel chromatography using heptanes/ethyl acetate (4:1) as the eluent, and 4.5 g of 2,2-dimethoxyethyl N-benzyloxycarbonyl-L-prolinate was obtained.

(f) 2,2-Dimethoxyethyl (−)-Menthoxyacetate

A 100 mL round bottom flask equipped with a magnetic stirrer is flushed with nitrogen for a period of 5 minutes. To the flask (−)-menthoxyacetic acid (9.5 g), 2,2-dimethoxyethanol (5.64 g), and dichloromethane (50 mL) are added and the mixture is cooled using an ice water bath (0–5° C.). DMAP (0.27 g) is added to the reaction mixture followed by the slow addition of DCC (9.6 g) over a period of 5 minutes. The resulting solid is filtered and washed with heptanes (3×15 mL). The organic filtrate is washed with 1N hydrochloric acid (15 mL), followed by water (25 mL) and brine (2×15 mL). The organic layer is dried over sodium sulfate, filtered and concentrated to give 13.82 g of 2,2-dimethoxyethyl (−)-menthoxyacetate.

(g) 2,2-Dimethoxyethyl N-Benzyloxycarbonyl-L-valinate

A 100 mL round bottom flask equipped with a magnetic stirrer and a nitrogen inlet is added N-benzyloxycarbonyl-L-valine (3.6 g), dichloromethane (25 mL), and 2,2-dimethoxyethanol (1.85 g) and the mixture is cooled using an ice bath (0–5° C.). DMAP (0.089 g) is added to the reaction mixture followed by the addition of DCC (3.6 g) over a period of 2 minutes. The suspended solid is filtered, the filter cake is washed with 3×10 mL of heptanes, and the filtrate is concentrated. The crude product is purified by silica gel chromatography (4:1, heptanes/ethyl acetate eluent) to provide 5.3 g of 2,2-dimethoxyethyl N-benzyloxycarbonyl-L-valinate.

Example 3

(a) (2R)-2-[(2'S)-2'-(Trimethylacetyloxy)phenylacetyloxymethyl]-1,3-oxathiolan-5-one (9)

The reactor is loaded with the ester acetal (8, $R_1=R_2=Me$) (3.9 kg) dissolved in toluene (24 L) and heated to about 60° C. Camphorsulfonic acid (0.39 kg, 10% w/w) followed by mercaptoacetic acid (4.5 kg) are added to the solution. The resulting mixture is heated at about 60° C. for 6 hours. After cooling to 20–25° C., the pH is adjusted to approximately 7.5 with saturated sodium bicarbonate (20 kg). The toluene phase is then washed with saturated sodium bicarbonate (2×5 kg), water (20 kg) and with a mixture of water (18 kg) and acetic acid (1.8 kg). The toluene phase is vacuum distilled to an oil. The oil is coevaporated with isopropanol (20 kg) three times to remove residual toluene. To the oil 1.5 volumes of isopropanol is added and warmed to 40–45° C. To the clear solution is added water and the batch is allowed to cool to room temperature. The suspension is further cooled to 0–5° C. over 6–7 hours. The crystals obtained are filtered and washed with isopropanol, and then vacuum dried at 45–50° C. The dried lactone (350 kg, 1:1, SR:SS diastereomeric ratio) is combined with 8 volumes of heptane/toluene (2/1, v/v) and stirred at room temperature for 6 hours. The suspended solid is collected by filtration to give 131.2 kg of product (9:1, SR:SS diastereomeric ratio). This mixture is suspended in heptane/toluene (2/1, v/v) and warmed to 65° C. to give a clear solution. The solution is allowed to cool and, at approximately 60° C., seeds (>98% SR) are added. The suspension is cooled at a rate of about 10° C./h to 30° C. and finally to 25° C. over about 1 hour. The solid is filtered to afford 107.6 kg of 9(97:3 SR:SS diastereomeric ratio).

$^1$H NMR (300 MHz, CDCl$_3$): 1.29 (s, 9H), 3.54 (s, 2H), 4.28–4.43 (m, 2H), 5.52–5.55 (m, 1H), 5.90 (s, 1H), 7.38–7.49 (m, 5H).

The conversion of compound 9 into a 1,3-oxathiolane nucleoside analogues, such as (−)-FTC and 3TC, may be accomplished, for example, using Scheme 3 of FIG. 3 or the like.

(b) (2R) and (2S)-2-[((S)-6-Methoxy-α-methyl-2-naphthalenacetyloxy)methyl]-1,3-oxathiolan-5-one To a round bottom flask is added 2,2-dimethoxyethyl (S)-6-methoxy-α-methyl-2-naphthaleneacetate (13.8 g), dichloroethane (60 mL), camphorsulfonic acid (0.7 g) and magnesium sulfate (1.0 g). The reaction mixture is heated to reflux and a solution of mercaptoacetic acid (13.5 g) in dichloroethane (15 mL) is added dropwise. The mixture is removed from the oil bath and a sample is taken for TLC and NMR analysis. Additional camphorsulfonic acid (0.6 g) is added and the mixture is heated in an oil bath to reflux for 2 hours. The mixture is cooled to room temperature and then shaken with water (50 mL) and saturated sodium bicarbonate (50 mL). The separated lower phase is shaken with saturated sodium bicarbonate (25 mL) and water (50 mL), the phases are separated and the lower cloudy organic phase is vacuum concentrated to give 17.4 g of crude product. The obtained syrup is applied to a silica column and eluted with EtOAc/heptanes (15:85) to provide 8.0 g of product.

(c) (2R) and (2S)-2-[(2S)-(Acetyloxy)phenylacetyloxy)methyl]-1,3-oxathiolan-5-one A 250 mL, single necked round bottom flask equipped with a stir bar and distillation set-up is charged with 2,2-diethoxyethyl (2S)-2-(acetyloxy)phenylacetate (10 g), toluene (100 mL) and mercaptoacetic acid (3.86 g). The mixture is heated to reflux at 105–110° C., stirred for 2–3 hours and cooled to 50–60° C. Toluenesulfonic acid (10 mg) is added to the mixture and the reflux is continued for 2 hours. The reaction mixture is cooled to room temperature (20–25° C.) and then washed with water (40 mL) and dried (Na$_2$SO$_4$), and concentrated. The crude product is purified on silica gel, eluting with heptanes/ethyl acetate (3:1) to provide 2.4 g of desired product.

(d) (2R) and (2S)-2-[(N-Benzyloxycarbonyl-L-prolinoyloxy)methyl]-1,3-oxathiolan-5-one A 100 mL, round bottom flask equipped with a reflux condenser and an addition funnel is purged with nitrogen for 5 minutes. To the flask 2,2-dimethoxyethyl N-benzyloxycarbonyl-L-prolinate (3.35 g), 1,2-dichloroethane (30 mL) and camphorsulphonic acid (0.34 g) are added and the mixture is heated using an oil bath to 35° C. A solution mercaptoacetic acid (3.7 g) in 1,2-dichloroethane (5 mL) is slowly added dropwise to the reaction mixture. The mixture is heated to 80° C. using an oil bath maintained at this temperature for about 2 hours. The reaction mixture is allowed to cool to room temperature and is then diluted with ethyl acetate (150 mL) and washed with saturated sodium bicarbonate (2×50 mL), water (25 mL) and brine (25 mL). The aqueous layers are combined, extracted with ethyl acetate (50 mL) and washed with water (25 mL) followed by brine (25 mL). The organic layers are combined, dried with sodium sulfate, filtered, and the filtrate is concentrated and dried under high vacuum overnight. The resulting crude product is purified by silica gel chromatography eluting with heptanes/ethyl acetate (4:1) to provide 3.0 g of product.

(e) (2R) and (2S)-2-[((−)-Menthoxyacetyloxy)methyl]-1,3-oxathiolan-5-one

A 100 mL, round bottom flask equipped with a reflux condenser, addition funnel and magnetic stirrer is purged with nitrogen for 5 minutes. To the flask 2,2-dimethoxyethyl (−)-menthoxyacetate (5.0 g), dichloroethane (40 mL) and camphorsulphonic acid (0.50 g) are added. The reaction is heated to about 80° C. and a solution of mercaptoacetic acid (6.1 g) in dichloroethane (10 mL) is added dropwise. After the addition, the reaction is maintained at about 80° C. for 1 hour. The reaction is allowed to cool to room temperature and is diluted with ethyl acetate (150 mL), washed with saturated sodium bicarbonate (2×50 mL), water (25 mL) and brine (25 mL). The combined aqueous layers are extracted with ethyl acetate (50 mL) and washed with water (25 mL) and brine (25 mL). The combined organic layers are dried (Na$_2$SO$_4$), concentrated and dried overnight under high vacuum to give 4.94 g of product.

(f) (2R) and (2S)-2-[(N-Benzyloxycarbonyl-L-valinoyloxy)methyl]-1,3-oxathiolan-5-one A 100 mL, round bottom flask equipped with an addition funnel and reflux condenser is flushed with nitrogen for 5 minutes. To the flask 2,2-dimethoxyethyl N-benzyloxycarbonyl-L-valinate (4.4 g), 1,2-dichloroethane (35 mL) and camphorsulphonic acid (0.44 g) are added and the mixture is heating to 32° C. using an oil bath. A solution of mercaptoacetic acid (4.92 g) in dichloroethane (5 mL) is added dropwise and the solution is heated at about 75° C. for one hour. The reaction mixture is allowed to cool to room temperature, diluted with ethyl acetate (150 mL) and washed with saturated sodium bicarbonate (2×50 mL) followed by water (25 mL) and brine (25 mL). The aqueous layers are combined and extracted with ethyl acetate (50 mL) and the separated organic layer is washed with water (25 mL) followed by brine (25 mL). The combined organic layers are dried (Na$_2$SO$_4$), filtered and concentrated, and dried under high vacuum overnight. The crude product is purified on silica gel, eluting with heptanes/ethyl acetate (4:1) to provide 2.95 g of product.

Example 4

(a) Recovery and Recycling of (2S)-2-[(2'S)-2'-(Trimethylacetyloxy)phenylacetyloxymethyl]-1,3-oxathiolan-5-one

To a 100 mL round bottom flask fitted with a reflux condenser and nitrogen inlet are added 2-(R,S)-2-[(2'S)-2'-(trimethylacetoxy)phenylacetyloxymethyl]-1,3-oxathiolan-5-one (5 g, 31:69, RS:SS diastereomeric ratio) and 40 mL of heptanes/toluene (2/1, v/v). To the resulting suspension, camphorsulfonic acid (0.25 g, 5% wt) and glacial acetic acid (3.4 g, 4 eq) are added with stirring. The mixture is stirred at about 60° C. The progress of the epimerization is monitored by $^1$H NMR spectroscopy. After 48 hours, the reaction mixture is cooled to room temperature and is washed with saturated sodium bicarbonate (2×30 mL), deionized water (10 mL) and 5% aqueous acet (10 mL). The organic layer is concentrated to give a semi-solid. The residue is dissolved in toluene (5 mL) and heptanes (30 mL) is added at approximately 45° C.

The clear solution is allowed to cool and is seeded with pure lactone. After 2–3 hours the suspension is further cooled using an ice-water bath. After 2–3 hours at 0–5° C., the solid is collected by filtration and vacuum dried to give 4.5 g of lactone (1:1, RS:SS diastereomeric ratio).

While the foregoing provides a detailed description of preferred embodiments of the invention, it is to be understood that this description is illustrative only of the principles of the invention and not limitative. Furthermore, as many changes can be made to the embodiments without departing from the scope of the invention, it is intended that all material contained herein be interpreted as illustrative of the invention and not in a limiting sense.

The embodiments of the invention in which an exclusive property or privilege is claimed are as follows:

1. A compound of formula A wherein R* represents an acyl radical of an acid selected from the group consisting of mandelic acid, menthoxyacetic acid, amino acids, camphorsulphonic acid, 2-(trimethylacetyloxy) phenylacetic acid, and 6-methoxy-α-methyl-2-naphthalene acetic acid.

2. A compound of formula 9

3. A process for the manufacture of the compound of formula A of claim 1, wherein R* represents an acyl radical of an acid selected from the group consisting of mandelic acid, menthoxyacetic acid, amino acid, camphorsulfonic acid, 2-(trimethyl acetyloxy) phenylactic acid, and 6-methoxy-α-methyl-2-naphthalene acetic acid, said process comprising X = H, halogen,
R₁, R₂ = alkyl, cycloalkyl, aryl, alkaryl, aralkyl

4. A process for the manufacture of a compound of formula 9 useful for conversion into an enantiomerically enriched 1,3-oxathiolane nucleoside analogue, comprising the reaction of mandelic acid with a compound of formula 4 wherein X is a leaving group to produce a compound of formula 5 and thereafter converting the compound of formula 5 into the compound of formula 9 in a substantially high purity, crystalline form.

5. The process of claim 4 wherein the conversion comprises the step of halogenation.

6. The process of claim 5 wherein the conversion comprises the step of esterification.

7. The process of claim 6 wherein the conversion comprises the step of lactonization.

8. The process of claim 7 wherein the conversion comprises the step of selective crystallization.

9. The process of claim 5, 6, 7, or 8 wherein the step of halogenation involves conversion of (2S)-2-(trimethylacetyloxy)phenylacetic acid into a (2S)-2-(trimethylacetyloxy) phenylacetyl halide; the step of esterification involves reacting the (2S)-2-trimethylacetyloxy) phenylacetyl halide with a 2,2-dialkoxyethanol compound to produce a 2,2-dialkoxyethyl (2S)-2-(trimethylacetyloxy) phenylacetate; the step of lactonization involves reacting the 2,2-dialkoxyethyl (2S)-2-(trimethyl-acetyloxy) phenylacetate intermediate with 2-mercaptoacetic acid to produce a mixture of (2R)-2-[(2'S)-2'-(trimethylacetyloxy) phenylacetyloxymethyl]-1,3-oxathiolan-5-one and (2S)-2-[(2'S)-2'-(trimethylacetyloxy)phenylacetyloxymethyl]-1,3-oxathiolan-5-one; and the step of selective crystallization involves the separation of (2R)-2-[(2'S)-2'-(trimethylacetyloxy)phenylacetyloxymethyl]-1,3-oxathiolan-5-one from (2S)-2-[(2'S)-2'-(trimethylacetyloxy) phenylacetyloxymethyl]-1,3-oxathiolan-5-one mixture to produce enantiomerically and diastereomerically enriched (2R)-2-[(2'S)-2'-(trimethylacetyloxy)phenylacetyloxy methyl]-1,3-oxathiolan-5-one.

10. The process of claim 4 wherein the compound of formula 4 is a trimethylacetyl halide.

11. The process of claim 10 wherein the trimethylacetyl halide is trimethylacetyl chloride.

12. The process of claim 9 wherein the (2S)-2-(trimethylacetyloxy)phenylacetyl halide is (2S)-2-(trimethylacetyloxy)phenylacetyl chloride.

13. (2R) and (2S)-2-[(2'S)-2'-(Trimethylacetyloxy) phenylacetyloxymethyl]-1,3-oxathiolan-5-one.

14. The process of claim 4 wherein the compound 9 produced is further converted to a 1,3oxathiolane nucleoside analogue.

15. The process of claim 14 wherein the 1,3-oxathiolane nucleoside analogue is selected from the group consisting of (−)-FTC and 3TC.

16. The process of claim 5 wherein the (2S)-2-[(2'S)-2'-(trimethylacetyloxy) phenylacetyloxymethyl]-1,3-oxathiolan-5-one, is recovered and recycled.

17. A process of preparing a 1,3-oxathiolane nucleoside analogue comprising the following:

18. The process of claim 3, wherein the configuration at the asymmetric carbon atom between oxygen and sulfur is (R) or (S).

19. The process of claim 3 further comprising the following:

recrystallization

* * * * *